United States Patent [19]
d'Ostrowick et al.

[11] 3,969,405

[45] *July 13, 1976

[54] OXIDATION OF ALKYLAROMATICS

[76] Inventors: Pierre M.J.G. de Radzitzky d'Ostrowick, 101, Ave. Paul Hymans; Jacques D. V. Hanotier, 36, Avenue Dr. Decroly, both of Brussels, Belgium

[*] Notice: The portion of the term of this patent subsequent to May 5, 1989, has been disclaimed.

[22] Filed: Apr. 11, 1972

[21] Appl. No.: 243,086

Related U.S. Application Data

[63] Continuation-in-part of Ser. No. 884,336, Dec. 11, 1969, Pat. No. 3,665,030.

[30] Foreign Application Priority Data

Sept. 17, 1971 France .............................. 71.33504

[52] U.S. Cl. ........................................... 260/524 M
[51] Int. Cl.$^2$ ........................................ C07C 51/33
[58] Field of Search ............................. 260/524 M

[56] References Cited
UNITED STATES PATENTS 3,665,030  5/1972  d'Ostrowick et al. ............... 260/488
3,678,105  7/1972  Croce et al. ..................... 260/524 R

FOREIGN PATENTS OR APPLICATIONS 727,874  4/1964  Belgium ............................ 262/524

OTHER PUBLICATIONS

Ohta et al., Kogyo Kagaku Zasshi, vol. 63, No. 5, 1960, pp. 768–763.

*Primary Examiner*—Anton H. Sutto
*Attorney, Agent, or Firm*—S. B. Wiczer

[57] ABSTRACT

Process of liquid phase oxidation of the alpha carbon atom of alkylbenzenes by a manganic or cobaltic salt and an acid activator with or without an oxidation-resistant solvent either in an inert atmosphere to produce lower oxidation products of the alpha carbon atom such as alcohols or their esters; or, in the presence of molecular oxygen, to produce higher oxidation products such as aromatic aldehydes, ketones or carboxyl acids.

15 Claims, No Drawings

OXIDATION OF ALKYLAROMATICS

The present invention relates to a process for selective oxidation of alkylaromatic compounds using an oxidizing system comprising a higher valent cobalt (III) or manganese (III) salt of a carboxylic acid and a relatively strong acid and this application is a continuation-in-part of my copending application, Ser. No. 884,336, filed Dec. 11, 1969, now U.S. Pat. No. 3,665,030, issued May 23, 1972.

Oxidation of alkylaromatic compounds into oxygenated products in the liquid phase with molecular oxygen in the presence of a heavy metal catalyst is the best available to the chemical industry at this time. Its application remains restricted as a rule to the production of the carboxylic acids. This is principally due to the fact that to reach a sufficient rate of reaction, stringent conditions such as high temperatures and pressures must be applied so that intermediate oxidation products of the alcohol, aldehyde or ketone type are rapidly converted into acids. During this process, the alkyl groups comprising several atoms of carbon undergo a cleavage of the carbon-carbon bonds except for the bond joining the side chain to the aromatic nucleus. For this reason, the method is applied principally for oxidation of methylaromatic hydrocarbons like toluene and xylenes. Oxidations performed in the art under milder conditions with various catalysts have been nonselective or inapplicable.

We have discovered that by employing an oxidizing system comprising the cobalt or manganese salt of a carboxylic acid in higher valent form annd a relatively strong acid, the oxidation of the alkylaromatic compounds can be performed at distinctly lower temperatures than those previously required, with a higher rate of reaction and a greatly improved selectivity. We have found that by appropriate selection of the components of the oxidizing system and of the operating conditions, the oxidation of the alkylaromatic compounds can be controlled to form side chain alcohols, mainly in the form of esters; or to form aromatic ketones or aldehydes, depending on the structures of the alkyl substituent; or to form aromatic carboxylic acids selectively as principal products. Analogously, starting with a polyalkylated aromatic compound, the reaction can be limited to selectively oxidize a single alkyl group or carried further to oxidize several alkyl side chains. Finally, the oxidizing system employed has an activity such that the alkylaromatic compounds further substituted by a deactivating group are attacked rapidly. Such deactivating groups are chloro, nitro, carboxyl or other electron-attracting groups.

The main object of the present invention is to provide a process for the oxidation of alkylaromatic compounds, during which one or more alkyl groups thereof are converted quickly in satisfactory yield into oxygenated functions, with a high degree of selectivity and control. It is a further object to provide a process of carrying out such oxidations at low temperatures. A further object is to provide an improved liquid phase oxidation of alkylaromatic and dialkyl aromatic and alkylaromatic compounds having more than two and up to six alkyl groups to form monocarboxylic aromatic acids and dicarboxylic aromatic acids as well as higher polycarboxylic aromatic acids.

According to the present invention, alkylaromatic compounds having at least one hydrogen atom at the alpha position to the aromatic nucleus are oxidized in the liquid phase at that alpha position at a temperature in the range of −30°C to +100°C, with an oxidizing system comprising the higher valent cobalt (III) or higher valent manganese (III) salt of a carboxylic acid and a stable acid whose dissociation constant is higher than $10^{-3}$, or boron trifluoride, or a mixture thereof.

The alkylaromatic compounds which are oxidized most satisfactorily by the process of the invention are those which comprise at least one alkyl radical having at least one hydrogen atom at the alpha position relative to the aromatic ring. Although higher alkyl radicals can be oxidized such as those having up to about 30 carbon atoms or even higher, the aromatic compounds with 1 to 6 alkyl radicals having from 1 to 4 carbon atoms are a preferred group of alkylaromatic compounds to be oxidized since they are easily and more economically available. Typical alkylaromatics oxidized herein are the mono-, di- and tri-alkylbenzenes, like toluene, ethylbenzene, cumene, o-, m- or p-xylenes, o-, m- or p-diethylbenzenes and trimethylbenzenes. Polynuclear alkyl-aromatic compounds such as the mono-, di- and trialkylnaphthalenes, like methyl naphthalenes, ethyl naphthalenes and dimethyl naphthalenes are also easily oxidized. Apart from these purely hydrocarbon compounds, alkylaromatic compounds substituted by other radicals such as chloro, bromo, iodo, fluoro, nitro or oxygenated radicals such as acyl, alkoxy, carboxyl, 1-acyloxyalkyl, may also be oxidized. Typical such substituted alkylaromatic compounds are p-chlorotoluene, p-bromoethylbenzene, m-nitrotoluene, o-acetyltoluene, 4-methoxyethylbenzene, p-toluic acid, 4-methyl-1-naphthoic acid, p-methylbenzyl acetate, and the like.

In order that the oxidation of these compounds by the process of the invention may be performed in the liquid phase, it is not essential but is often useful to employ a solvent. In particular cases the oxidizing system is soluble in the liquid alkylaromatic compound to be oxidized, and the reaction can occur in the solution thus obtained. Most frequently, however, the reactants are desirably dissolved in the solvent common to both. In general any liquid reasonably inert to oxidation, in which the alkylaromatic compound to be oxidized and the oxidizing system are soluble, may be used. The fatty acids containing from 2 to 10 carbon atoms and their lower esters, preferably their methyl and t-butyl esters satisfactorily fulfill the preceding conditions. Acetic acid is a particularly advantageous solvent.

Among the metal compounds capable of oxidizing hydrocarbon or other organic substances, the cobalt (III) and manganese (III) salts of carboxylic acids are preferred. They are powerful oxidizers; they are satisfactorily soluble in such organic solvents; and they are easily produced by known methods. From these points of view, the cobalt (III) and manganese (III) salts of fatty acids containing from 2 to 10 atoms of carbon, and preferably their acetates, are particularly satisfactory. For example, cobalt (III) acetate may be produced by co-oxidation of cobalt (II) acetate with acetaldehyde in acetic acid in the presence of oxygen. Manganese (III) acetate may be produced by oxidation of manganese (II) acetate with potassium permanganate in acetic acid. The cobalt (III) and manganese (III) salts of the other fatty acids can be produced in analogous manner or by exchange reaction between these and cobalt (III) acetate.

A fundamental and important aspect of the present invention is the discovery that the oxidizing power of these cobaltic and manganic salts in respect of alkylaromatic compounds is enhanced considerably by the presence of a relatively strong inorganic or organic acid. The acids which display this activating effect are those whose dissociation constant K is higher than $10^{-3}$. They should be soluble in the reaction medium and should not interfere with the reaction. Suitable acids are sulphuric acid ($K_1$ 1), perchloric acid (K 1), p-toluenesulphonic acid (K 1), trifluoroacetic acid (K = $6.10^{-1}$), trichloroacetic acid (K = $2.10^{-1}$), dichloroacetic acid (K = $3.3 \times 10^{-2}$), phosphoric acid ($K_1 = 7.5 \times 10^{-3}$), and monochloroacetic acid (K = $1.4 \times 10^{-3}$). Some Lewis acids such as boron trifluoride, also have an activating action. The acids containing chlorine, bromine or iodine in ionic form, such as hydrochloric acid, hydrobromic acid or aluminum trichloride are unstable in the conditions of the process and should be avoided. Particularly in the preparation of polycarboxylic aromatic acids, it is preferred to use a cobaltic salt in high concentration in the presence of a perfluorinated compound having from 2 to 10 carbon atoms such as a perfluorinated carboxylic acid.

The activating action of the acids defined above is exerted both on the rate and the progress of the reaction. The effect is the more pronounced the stronger the acid and, up to a definite limit, the higher its concentration. On the other hand, the quantity of acid should be correlated to the quantity of cobaltic or manganic salt employed. For example, if sulphuric acid is employed to activate a cobaltic salt, a molar ratio between acid and salt of approximately 2 is needed to reach maximum activity. With an acid of lesser strength, such as trichloroacetic acid, a ratio from 5 to 20 is preferable. Although the mechanism of the activation has not been clarified yet, the facts which have been set forth lead to the possibility that the cobaltic or manganic salt reacts with the acid to produce a more oxidizing species which is assumed to be principally responsive to the attack of the substrate. The following scheme can be envisaged accordingly, where the acid, the metal salt, and the reactive species are represented respectively by AH, $M^{3+}$ and M(III):

AH A⁻ + H⁺     (1)

M³⁺ + H⁺ M(III)     (2)

It must be added, moreover, that the activating effect of a given acid can vary with temperature, the nature of the metal salt and the reactivity of the substrate. For example, the activating action of weaker acids such as trichloroacetic acid or manganic acetate is less effective, under identical conditions, than on cobaltic acetate; but, at increased temperature, it is improved the more effectively with the more reactive substrate. These different factors should be taken into account in selecting the oxidizing system and the conditions to apply to oxidize a particular substrate.

The activator allows the oxidation of alkylaromatics to be performed at low temperature, more specifically within a temperature range of −30°C to +100°C. In order that the reaction may be rapid as well as selective, it is preferable to operate at temperatures between 0° and 60°C. The reaction will frequently be too slow below 0°C, and the selectivity inadequate above 60°C.

The nature of the oxidation products obtained by the present process is determined by the structure of the alkyl substituent, the composition of the oxidizing system, and the operating conditions. To produce alcohols in the form of esters, the reaction will be carried out in a carboxylic solvent such as acetic acid and in the absence of oxygen. For example, in these conditions, ethylbenzene can be converted almost quantitatively into the acetate of alpha-methylbenzyl alcohol by use of an oxidizing system comprising a manganic or a cobaltic salt. The ester obtained may then be hydrolyzed to produce the corresponding alcohol, or pyrolyzed to product styrene. Toluene is converted into benzyl acetate using the same conditions. In contrast, if it is preferred to obtain products containing a carbonyl function, it is advisable to operate in the presence of oxygen and to make provision for vigorous stirring of the reaction mixture. In these conditions, ethylbenzene can be converted into acetophenone by preferential use of an oxidizing system comprising a cobaltic salt. Analogously in the presence of oxygen, toluene can be oxidized into benzaldehyde or benzoic acid, depending on whether a manganic or cobaltic salt is employed. These particular examples clearly demonstrate the extraordinary selectivity of the process of the invention and the high degree of control it provides by simple selection of the oxidizing system and of the operating conditions.

The effect of oxygen exemplified by the above examples is another important aspect of the present invention. The manner in which oxygen operates in the reaction is not known with certainty. In the prior processes in which a compound of a metal of high valency is employed as an oxidant, oxygen does not as a rule have an appreciable effect on the reaction. In the present case it seems that the primary attack of the alkylaromatic compound leads to the formation of a free radical (reaction 3) which would then react with oxygen (reaction 4) to produce a peroxy radical which is subsequently convertible to produce a ketone, an aldehyde or even an acid, as the case may be. In the absence of oxygen, the radical would be oxidized in its turn, probably while producing a carbonium salt (reaction 5) which, in the presence of a carboxylic acid, would result in an ester (reaction 6).

RH + M(II) R° + M²⁺ + H⁺     (3)

R° + O₂ ROO° ketone, aldehyde or acid     (4)

R° + M(III) R⁺ + M²⁺     (5)

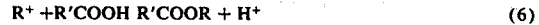

R⁺ +R'COOH R'COOR + H⁺     (6)

Corresponding to this pattern, the proportion of ester functions and of carbonyl functions in the reaction products is the result of competition between reactions (4) and (5). It will then be understood that to promote the production of compounds having a carbonyl function, it is necessary to choose conditions allowing the reaction (4) to predominate; that is, to operate in the presence of a gaseous phase containing oxygen and to make provision for vigorous stirring for rapid diffusion of the same into the liquid phase. This gaseous phase may consist of pure oxygen or of a mixture of oxygen with other gases which are inert in the conditions of the reaction such as air. The partial oxygen pressure may be between 0.1 and 50 atmospheres. In particular cases, it is possible to apply pressures lying outside this range. For example, a lower pressure than 0.1 atmosphere can be sufficient occasionally, subject to the condition of providing particularly effective stirring. On the other hand, higher pressures than 50 atmospheres may be applied, but these do not lead to an improvement in the results justifying additional plant investment costs. In the greater number of cases, an oxygen pressure of the order of 0.2 to 10 atmospheres will suffice to secure a high degree of conversion into products having a carbonyl function.

The quantity of oxidant to be employed depends on the degree of conversion required and on the nature of the products it is desired to obtain. The preceding pattern shows that at least two molar equivalents of higher valent metal salts are needed to produce an ester in a high yield from a monoalkylbenzene. It might be expected that a greater quantity of oxidant would be consumed to produce a ketone, an aldehyde or an acid. In reality the production of these compounds by the process of the invention requires no more than a small quantity of oxidant. For example, the production of acetophenone by oxidation of ethylbenzene by means of the system consisting of cobaltic acetate and trichloroacetic acid in the presence of oxygen requires no more than 1.5 to 2.2 atoms of cobalt (III) per molecule of hydrocarbon. In the same conditions 0.3 to 0.5 atom of cobalt (III) suffices to convert one molecule of toluene into benzoic acid. These small values demonstrate that a definite degree of regeneration of the oxidizing system occurs in the presence of oxygen, so that the quantity of oxidant consumed may in particular cases be smaller than the quantity of product formed.

In the case of polyalkyl aromatic compounds, the oxidation may be limited to a single alkyl group, or extended to several. It is plain to one skilled in the art that to limit the oxidation it is appropriate to shorten the period of reaction and to employ an excess of polyalkyl benzene in comparison with the oxidizing system, whereas the inverse of these conditions will be preferable if it is desired to oxidize several alkyl groups within one and the same molecule.

In the oxidation of o-xylene by the described procedure using molecular oxygen, the main product is o-toluic acid and the yield in phthalic acid is generally negligible. Similarly, when the same processes are applied to other aromatic compounds having methyl groups on vicinal nuclear carbon atoms i.e. pseudocumeme or durene, the reaction is generally limited to the oxidation of one or two non-adjacent methyl groups. For instance, when pseudocumene is oxidized in acetic acid with cobalt as catalyst and methylethylketone as initiator, there is obtained a mixture of 2-methylterephthalic and 4-methylisophthalic acids. And when the same method is applied to durene, there is obtained a mixture of 2,5-dimethylterephthalic and 4,6-dimethylisophthalic acids. Thus, in the liquid phase oxidation of such hydrocarbons having methyl substituents on vicinal nuclear carbon atoms, there is apparently some auto-inhibition phenomenon which precludes complete conversion of all methyl substituents into carboxyl groups.

In preferred preparation of a polycarboxylic aromatic acid there is provided a process for the preparation of aromatic polycarboxylic acids having at least two carboxyl groups on vicinal nuclear carbon atoms from methylaromatic compounds having at least one methyl substituent on a nuclear carbon atom vicinal to another nuclear carbon atom substituted by a radical selected from the group consisting of methyl, hydroxymethyl, formyl and carboxyl, which comprises reacting said methylaromatic compounds in acetic acid with a cobaltic salt at a concentration of at least 0.1 mole per liter of reaction mixture, the ratio of cobaltic ions to total cobalt being maintained above 0.5, in the presence of a perfluorinated saturated compound having from 2 to 10 carbon atoms, the molar ratio of said perfluorinated compound to said cobaltic salt being at least 1, at a temperature ranging from 40° to 100°C and in the presence of molecular oxygen at a partial pressure of from 0.2 to 20 atmospheres.

The perfluorinated saturated compounds having from 2 to 10 carbon atoms which can be used in accordance with the present invention may be perfluorinated carboxylic acids wherein all the hydrogen atoms except those which are part of a carboxyl group are substituted by fluorine atoms, these acids being used in free form. Specific examples of such acids are trifluoroacetic acid, pentafluoropropionic acid, heptafluorobutyric acid, perfluorocaprylic acid and the like. Also comprised in the above definition are cyclic acids such as perfluorocyclohexylacetic acid and dibasic acids such as perfluorosuccinic or perfluoroglutaric acids. Although some other perhalogenated acids such as trichloroacetic acid may on some occasions be used with advantage for the same purpose, the perfluorinated acids as above defined are preferred for their superior performances and their outstanding inertness in oxidizing media.

For the present process to be carried out in the liquid phase, it is not always necessary to use a solvent. Perfluorinated acids such as just defined have themselves excellent dissolving properties and, provided they are in the liquid state at the operating temperature, they may be used as a solvent for both the methylaromatic compound and the cobaltic salt. However, in most cases, it will be preferred for economic reasons to use an extraneous solvent. Acetic acid which is cheap, easily available and substantially resistant to oxidation is particularly suitable for this purpose.

The cobaltic salt which is used in the process may be any cobaltic salt which is sufficiently soluble in the reaction mixture to reach the desired concentration of at least 0.1 and preferably at least 0.2 mole per liter. The cobaltic salt of most aliphatic carboxylic acids fulfill this condition and as acetic acid is generally used as a solvent, cobaltic acetate is particularly suitable. The cobaltic salt may also be supplied as the salt of a perfluorinated acid as used in the process. Obviously, it is within the scope of the invention to supply both cobalt and perfluorinated acid as a cobaltic salt of the latter.

It has been discovered that when a perfluorinated compound such as defined above is present in a molar ratio of at least 1 with respect to the cobaltic salt, the oxidation of methylaromatic compounds having at least one methyl substituent vicinal to another methyl or to a hydroxymethyl, formy or carboxyl group by said cobaltic salt in the temperature range as specified hereinbefore proceeds with an enhanced rate to produce the corresponding polycarboxylic acids in almost quantitative yield. The high yields obtained in these conditions may be ascribed to the fact that, unexpectedly, the overoxidation which takes place to some extent when the cobaltic salt is used alone is completely suppressed by the presence of perfluorinated compounds even when the reaction is carried out for extended periods of time at a relatively high temperature e.g. above 80°C.

A further important advantage of the use of perfluorinated compounds according to the present invention is the fact that aromatic acids having carboxyl groups on vicinal positions are obtained in free form instead of in the form of cobalt complexes as observed when the cobaltic oxidizing salt is used alone. The free acids can therefore be recovered directly from the reaction mixture by known means such as by filtration or centrifugation without any further treatment except washing with a solvent, preferably acetic acid, to remove adhering components of the reaction mixture. The liquor from this recovery procedure will contain the whole of the cobaltic salt and perfluorinated acid originally present in the reaction mixture. It may therefore be recycled, eventually after volume adjustment, into the reaction zone and admixed therein with fresh substrate for further oxidation. Prior to recycling it is preferred to remove water of reaction from said liquor, although water contents up to 10 volume percent or even more in the reaction mixture may be tolerated.

These different operations may be conducted bathwise or continuously, the continuous mode of operation being preferred. In operating the process, the conditions may be so chosen as to ensure extensive or only partial conversion of the starting methylaromatic compound into the desired polycarboxylic acid. In the latter case, substantial amounts of intermediate oxidation products will obviously be present in the liquor from the product recovery procedure mentioned above and will need to be recycled. This mode of operation is advantageous as it generally provides higher rates of production, by sustaining active oxidation in the reaction zone. In both cases, overall molar yields of 90% or more in the desired polycarboxylic acid are generally achieved.

Such results are obtained in a temperature range of from 40 to 100°C, preferably from 50 to 90°C. The fact that even those methylaromatics having more than two methyl substituents on vicinal nuclear carbon atoms are converted in high yield at such low temperature into carboxylic acids having more than two carboxyl groups similarly situated is a surprising feature of the present invention; indeed, most of the liquid phase processes of the prior art wherein cobalt and/or another heavy metal is used as catalyst as ineffective for the same end at temperatures higher than 100°C and even higher than 200°C. This difference may be ascribed to the fact that in the conditions of the present invention the reaction does not proceed according to a radical chain process but rather through a mechanism involving direct electron abstraction from the substrate by the cobaltic ions and simultaneous reduction of the latter into their cobaltous form as shown in the following equation (2):

Co(III) + RH    Co(II) + R' + H⁺

In this case, the cobaltic salt does not work as a catalyst to promote initiation as illustrated by equation (1) but actually as a reactant. An indirect evidence for this explanation is the fact that perfluorinated acids as used in the present process promote the reaction whereas it is known that strong acids have an inhibitory effect on radical chain oxidations. As further evidence is the fact that when oxygen is omitted in the present process, effective reduction of cobalt (III) is still observed with simultaneous formation of oxidation products such as esters.

However, for oxidizing efficiently methylaromatic compounds into carboxylic acids as required for most practical applications, molecular oxygen must be supplied into the reaction zone. Pure oxygen or any oxygen containing gas such as air may be used for this purpose. In most cases, partial pressures of oxygen of from 0.2 to 20 atmospheres or more will ensure the methyl substituents to be transformed into carboxyl groups with negligible production of compounds having other oxygenated substituents such as formyl or hydroxymethyl groups.

Since the cobaltic salt works in the present process as a reactant and not as a catalyst, it is reduced as the reaction proceeds into its lower valency state so that, even when starting with a high concentration of cobaltic ions, this concentration would rapidly fall below the limit required for active oxidation. To achieve high yields in the desired polycarboxylic acids it is therefore necessary to maintain a high concentration of cobaltic ions by reoxidizing the cobaltous species produced as a result of the reaction. This can be made continuously or intermittently, in the reaction vessel or separately, known means e.g. by anodic oxidation or by chemical agents such as ozone or peroxide compounds or still by co-oxidation with an aldehyde. A particularly convenient method is to supply continuously acetaldehyde into the reaction zone at such a controlled rate as to maintain the desired level in cobaltic ions. Preferably the ratio of cobaltic ions to total cobalt will be maintained above 0.5, still preferably above 0.6.

The perfluorinated compound activator may be applied successfully to the oxidation of any methylaromatic compound wherever the methyl substituents are situated. For instance, it may be used to oxidize p-xylene into terephthalic acid; m-xylene into isophthalic acid; or mesitylene into trimesic acid. However, as those skilled in the art will understand from the foregoing description, it is especially useful for the oxidation of those hard-to-oxidize aromatic compounds which bear at least one methyl substituent on a nuclear carbon atom vicinal to another nuclear carbon atom substituted by a radical selected from the group consisting of methyl, hydroxymethyl, formyl and carboxyl. Specific examples of such compounds are o-xylene, pseudocumene, hemimellitene, durene, prehnitene, isodurene, pentamethylbenzene, hexamethylbenzene and oxidation intermediates thereof such as o-methylhydroxymethylbenzene, o-tolualdehyde, o-toluic acid, 2-methylterephthalic acid, 4,6-dimethylisophthalic acid and the like, further substituted or not by alkyl groups other than methyl or still by non-oxidizable radicals such as nitro, chloro or bromo. By selecting the proper conditions e.g. reaction time and temperature, such compounds are readily converted in almost quantitative yield into polycarboxylic acids having at least two carboxyl groups on vicinal nuclear carbon atoms. For instance, o-xylene can be converted into phthalic acid, psuedocumene into trimellitic acid and durene into pyromellitic acid. Such polycarboxylic acids are known to be of particular value as intermediates in the manufacture of high-performance plasticizers, coatings, films and fibers.

The invention will now be further described with reference to the following examples:

EXAMPLE I

This example illustrates the effect of sulfuric acid on the oxidizing power of manganic acetate with respect to alkylaromatic compounds.

A solution containing 0.20 mol/liter of m-diethylbenzene and 0.04 mol/liter of manganic acetate in acetic acid was heated to 70°C for 30 minutes. In a second assay, sulphuric acid was added to the solution at the concentration of 0.5 mol/liter, after which this solution was kept at 25°C for 10 minutes. A third assay was also carried out in the presence of sulphuric acid but in the absence of substrate. At the end of the three assays the manganic ions present in the solution were determined by cerimetry. The results obtained are given in the following table:

| Substrate (0.20M) | H$_2$SO$_4$ (0.5M) | Temperature (0°C) | Time (min) | Reduced Mn(III) % |
|---|---|---|---|---|
| + | − | 70 | 30 | 3 |
| + | + | 25 | 10 | 97 |
| − | + | 25 | 10 | 2 |

It is apparent that, in the presence of sulphuric acid, the oxidation of m-diethylbenzene by manganic acetate results in the almost complete reduction of the same in 10 minutes at 25°C, whereas in the absence of sulphuric acid, no appreciable reaction occurs in distinctly more severe conditions. The third assay adequately demonstrates that the effect of the activator is linked with the presence of m-diethylbenzene.

EXAMPLE II

This example illustrates the effect of trichloroacetic acid on the oxidizing power of cobaltic acetate in respect of alkylaromatic compounds. A solution containing 0.20 mol/liter of 2-ethylnaphthalene and 0.05 mol/liter of cobaltic acetate in acetic acid was kept at 25°C under a nitrogen atmosphere at atmospheric pressure for 15 minutes. The same assay was repeated after addition of trichloroacetic acid to the solution, in the proportion of 1.5 mol/liter. A third assay was also carried out in the presence of trichloroacetic acid, but in the absence of substrate. At the end of the three assays the cobaltic ions present in the solution were determined by cerimetry. The results obtained are given in the following table:

| substrate (0.2M) | trichloroacetic acid (1.5M) | reduced Co(III) (%) |
|---|---|---|
| + | − | 2 |
| + | + | 96 |
| − | + | 1 |

It is apparent that in the presence of trichloroacetic acid the oxidation of 2-ethylnaphthalene by means of cobaltic acetate results in the almost complete reduction of the same, whereas no appreciable reaction occurs in the absence of the acid activator. The third assay adequately shows that its action is linked to the presence of the hydrocarbon.

EXAMPLE III

This example illustrates the oxidation of toluene by means of the system consisting of manganic acetate and sulphuric acid.

A solution containing 0.10 mol/liter of toluene, 0.21 mol/liter of manganic acetate and 1.0 mol/liter of sulphuric acid in acetic acid, was kept at 25°C, without stirring, under a nitrogen atmosphere at atmospheric pressure. 78 per cent of the manganic ions had been reduced after 1 hour. An aliquot part of the reaction mixture was diluted with ether and then treated at 0°C with anhydrous sodium carbonate until the acidity was neutralized. The ether solution was analyzed by vapour phase chromatography to establish the composition of the neutral oxidation products. The acid products were identified by analysis of another aliquot part of the reaction mixture. The combined results of both analyses show that 54 per cent of the toluene employed had been converted to yield the following oxidation products whose relative proportions are expressed as molar percentages:

| | |
|---|---|
| benzyl alcohol (mainly in the form of its acetate ester) | 74 % |
| benzaldehyde | 25 % |
| benzoic acid | 1 % |

EXAMPLE IV

This example illustrates the effect of oxygen on the oxidation of toluene by means of the oxidizing system employed in the preceding example.

The experiment of Example III was repeated, but this time while stirring the reaction mixture in the presence of pure oxygen at atmospheric pressure. By treating and analyzing the reaction mixture as in Example III, it was established that 65% of the toluene employed had been converted to yield the following oxidation products whose relative proportions are expressed as molar percentages:

| | |
|---|---|
| benzaldehyde | 71 % |
| benzyl alcohol (mainly in the form of its acetate ester) | 24 % |
| benzoic acid | 5 % |

Comparing the results of this example to those of Example III, it is plain that in the presence of oxygen, toluene is converted preferentially into benzaldehyde rather than into benzyl alcohol.

EXAMPLE V

This example illustrates the oxidation of toluene by means of the system consisting of cobaltic acetate and trichloroacetic acid, in the presence of oxygen.

A solution containing 0.10 mol/liter of toluene, 0.20 mol/liter of cobaltic acetate and 1.5 mol/liter of trichloroacetic acid in acetic acid was stirred at 25°C in the presence of pure oxygen at atmospheric pressure. 16% of the cobaltic ions had been reduced after 4 hours. The reaction mixture was then treated and analyzed as in Example III. It was found that 81% of the toluene employed had been converted into pure benzoic acid.

In another experiment performed in identical manner but while extending the reaction period to 24 hours, the conversion of toluene into benzoic acid rose to 92%.

From this data it is calculated that the formation of a molecule of benzoic acid required the reduction of no more than 0.3 atom of cobalt, which demonstrates that a substantial proportion of the oxidant is regenerated in situ during the reaction.

EXAMPLE VI

This example illustrates the use of propionic acid as a solvent.

The experiment of the preceding example was repeated, while replacing acetic acid with propionic acid. Analysis of the reaction mixture after 24 hours showed that 55% of the toluene employed had been converted mainly to yield benzoic acid (98%) and small quantities of benzaldehyde (2%)

Identical results were obtained by replacing cobaltic acetate with cobaltic propionate.

EXAMPLE VII

This example illustrates the oxidation of ethylbenzene by means of the system consisting of manganic acetate and sulphuric acid.

A solution containing 0.10 mol/liter of ethylbenzene, 0.19 mol/liter of manganic acetate and 1.0 mol/liter of sulphuric acid in acetic acid was kept at 25° C, without stirring, under a nitrogen atmosphere at atmospheric pressure. 67% of the manganic ions had been reduced after 1 hour. The reaction mixture was then treated and analyzed as in Example III. It was thus established that 56% of the ethylbenzene employed had been converted to yield the following oxidation products whose relative proportions are expressed as molar percentages.

| | |
|---|---|
| alpha-methylbenzyl alcohol (mainly in the form of its acetate ester) | 93 % |
| acetophenone | 7 % |
| benzoic acid | 0 % |

EXAMPLE VIII

This example illustrates the oxidation of ethylbenzene by means of the system consisting of cobaltic acetate and trifluoroacetic acid.

A solution containing 0.10 mol/liter of ethylbenzene, 0.20 mol/liter of cobaltic acetate and 1.4 mol/liter of trifluoroacetic acid in acetic acid was kept at 25° C, without stirring, under a nitrogen atmosphere at atmospheric pressure. 77% of the cobaltic ions had been reduced after 24 hours. The reaction mixture was then treated and analyzed as in Example III. It was thus established that 56% of the ethylbenzene employed had been converted to yield the following oxidation products whose relative proportions are expressed as molar percentages.

| | |
|---|---|
| alpha-methylbenzyl alcohol (mainly in the form of its acetate esters) | 86 % |
| acetophenone | 9 % |
| benzoic acid | 5 % |

By operating in identical manner but omitting the addition of trifluoroacetic acid to the system, only 9% of the ethylbenzene was converted to yield the following products:

| | |
|---|---|
| alph-methylbenzyl alcohol | 0 % |
| acetophenone | 67 % |
| benzoic acid | 33 % |

It is plain that in the absence of the acid activator, the reaction is not only slowed down considerably, but its selectivity is completely changed.

EXAMPLE IX

This example illustrates the oxidation of ethylbenzene by means of the system consisting of cobaltic acetate and boron trifluoride.

The experiment of Example VIII was repeated, but trifluoroacetic acid was replaced by boron trifluoride in the same concentration. Analysis of the reaction mixture after 3 hours showed that 27% of the ethylbenzene employed had been converted to yield the following oxidation products whose relative proportions are expressed as molar percentages:

| | |
|---|---|
| alpha-methylbenzyl alcohol (mainly in the form of its acetate ester) | 87 % |
| acetophenone | 5 % |
| benzoic acid | 8 % |

By operating in identical manner, but without adding boron trifluoride to the system, only 5% of the hydrocarbon had been converted to yield the following products:

| | |
|---|---|
| alpha-methylbenzyl alcohol | 0 % |
| acetophenone | 60 % |
| benzoic acid | 40 % |

The action of the activator set forth in the preceding example is confirmed in every respect by these results.

EXAMPLE X

This example illustrates the oxidation of ethylbenzene by means of the system consisting of cobaltic acetate and p-toluenesulphonic acid.

The experiment of Example VIII was repeated but trifluoroacetic acid was replaced with p-toluenesulphonic acid at the concentration of 0.3 mol/liter. 33% of the cobaltic ions had been reduced after 24 hours, and analysis showed that 14% of the ethylbenzene employed had been converted to yield the following oxidation products whose relative proportions are expressed as molar percentages:

| | |
|---|---|
| alpha-methylbenzyl alcohol (mainly in the form of its acetate ester) | 75 % |
| acetophenone | 15 % |
| benzoic acid | 10 % |

EXAMPLE XI

This example illustrates the oxidation of ethylbenzene by means of the system consisting of cobaltic acetate and trichloroacetic acid.

The experiment of Example VIII was repeated but trifluoroacetic acid was replaced with trichloroacetic acid at the same concentration. 25 % of the cobaltic ions had been reduced after 30 minutes, and analysis showed that 17 % of the ethylbenzene employed had been converted to yield the following oxidation products whose relative proportions are expressed as molar percentages :

| | |
|---|---|
| alpha-methylbenzyl alcohol (mainly in the form of its acetate ester) | 88 % |
| acetophenone | 9 % |
| benzoic acid | 3 % |

EXAMPLE XII

The experiment of Example XI was repeated, but operating at 60°C instead of 25°C. 66 % of the cobaltic ions had been reduced after 30 minutes, and analysis showed that 40 % of the ethylbenzene employed had been converted to yield the following oxidation products whose relative proportions are expressed as molar percentages:

| | |
|---|---|
| alpha-methylbenzyl alcohol (mainly in the form of its acetate ester) | 86 % |
| acetophenone | 7 % |
| benzoic acid | 7 % |

Compared to those of Example XI, these results show that an increase in the temperature can speed up the reaction without appreciably changing its selectivity.

EXAMPLE XIII

This example illustrates the effect of oxygen on the oxidation of ethylbenzene by means of the oxidizing system employed in Examples XI and XII.

A solution containing 0.10 mol/liter of ethylbenzene, 0.20 mol/liter of cobaltic acetate and 1.5 mol/liter of trichloroacetic acid in acetic acid was stirred at 25°C in the presence of pure oxygen at atmospheric pressure. 62 % of the cobaltic ions had been reduced after 4 hours. The reaction mixture was then treated and analyzed as in Example III. It was thus established that 67 % of the ethylbenzene had been converted to yield the following oxidation products whose relative proportions are expressed as molar percentages:

| | |
|---|---|
| acetophenone | 79 % |
| alpha-methylbenzyl alcohol (partially in the form of its acetate ester) | 15 % |
| benzoic acid | 6 % |

By comparing these results to those of Examples XI and XII, it is plain that in the presence of oxygen, ethylbenzene is converted mainly into ketone rather than into alcohol.

EXAMPLE XIV

The experiment of Example XIII was repeated, but on this occasion operating under an oxygen pressure of 10 kg/cm2. Analysis of the reaction mixture after 4 hours showed that 48 % of the ethylbenzene employed had been converted to yield the following oxidation products whose relative proportions are expressed as molar percentages:

| | |
|---|---|
| acetophenone | 84 % |
| alpha-methylbenzyl alcohol (partially in the form of its acetate ester) | 16 % |
| benzoic acid | undetectable |

By comparing these results to those of Example XIII, it is apparent that the proportion of acetophenone has been increased slightly by operating under a higher oxygen pressure. No additional increase is observed, however, if the test is performed under an oxygen pressure of 30 kg/cm2.

EXAMPLE XV

This example illustrates the use of methyl acetate as a solvent.

A solution containing 0/.10 mol/liter of ethylbenzene, 0.21 mol/liter of cobaltic acetate and 1.5 mol/liter of trichloroacetic acid in methyl acetate was kept at 25°C, without stirring, under a nitrogen atmosphere at atmospheric pressure. 44 % of the cobaltic ions had been reduced after 5 hours. The reaction mixture was then treated and analyzed as in Example III. It was thus established that 14 % of the ethylbenzene employed had been converted to yield the following oxidation products whose relative proportions are expressed as molar percentages:

| | |
|---|---|
| alpha-methylbenzyl alcohol (mainly in the form of its acetate ester) | 73 % |
| acetophenone | 22 % |
| benzoic acid | 5 % |

By operating in analogous manner but in the presence of pure oxygen instead of an atmosphere of nitrogen, acetophenone becomes the principal product.

EXAMPLE XVI

This example illustrates the use of t-butyl acetate as a solvent.

The experiment of Example XV was repeated while replacing methyl acetate with t-butyl acetate. 45 % of the cobaltic ions had been reduced after 3 hours, and analysis showed that 11 % of the ethylbenzene employed had been converted to yield the following oxidation products whose relative proportions are expressed as molar percentages:

| | |
|---|---|
| alpha-methylbenzyl alcohol (mainly in the form of its acetate ester) | 82 % |
| acetophenone | 18 % |

EXAMPLE XVII

This example illustrates the use of pelargonic acid as a solvent.

A solution containing 0.51 mol/liter of ethylbenzene, 0.17 mol/liter of cobaltic acetate and 1.5 mol/liter of trichloroacetic acid in pelargonic acid was kept at 25°C, without stirring, under a nitrogen atmosphere at atmospheric pressure. 78 % of the cobaltic ions had been reduced after 24 hours. The reaction mixture was then neutralized by means of alcoholic potash and subjected to saponification for 4 hours in such manner as to hydrolyze the pelargonic esters formed during the reaction, to facilitate the identification of the oxidation products of ethylbenzene. After filtering the insoluble salts, the alcoholic solution thus obtained was analyzed directly by vapor phase chromatography. The analysis enabled to identify the following oxidation products whose relative proportions are expressed as molar percentages:

| | |
|---|---|
| alpha-methylbenzyl alcohol | 83 % |
| acetophenone | 17 % |

EXAMPLE XVIII

This example illustrates the possibility of not employing any solvent.

A solution containing 0.2 mol/liter of cobaltic acetate and 1.5 mol/liter of trichloroacetic acid in ethylbenzene was kept at 25°C, without stirring, under a nitrogen atmosphere at atmospheric pressure. 59 % of the cobaltic ions had been reduced after 30 minutes. Analysis of the reaction mixture by a method analogous to that described in Example III enabled to identify the following oxidation products whose relative proportions are expressed as molar percentages :

| | |
|---|---|
| acetophenone | 67 % |
| alpha-methylbenzyl alcohol | 31 % |
| alpha-methylbenzyl acetate | 2 % |
| benzoic acid | 0 % |

This example also shows that, in the absence of a carboxylic solvent, the formation of ester is negligible, as in the presence of oxygen.

EXAMPLE XIX

This example illustrates the oxidation of cumene by means of the system consisting of cobaltic acetate and trichloroacetic acid in the presence of oxygen.

A solution containing 0.10 mol/liter of cumene, 0.20 mol/liter of cobaltic acetate and 1.5 mol/liter of trichloroacetic acid in acetic acid, was stirred at 25°C in the presence of pure oxygen at atmospheric pressure. 54 % of the cobaltic ions had been reduced after 24 hours. The reaction mixture was then treated and analyzed as in Example III. It was thus established that 21 % of the cumene employed had been converted to yield the following oxidation products whose relative proportions are expressed as molar percentages :

| | |
|---|---|
| acetophenone | 75 % |
| alpha, alpha-dimethylbenzyl alcohol | 10 % |
| benzoic acid | 15 % |

EXAMPLE XX

This example illustrates the oxidation of 2-ethylnaphthalene by means of the system consisting of cobaltic acetate and trichloroacetic acid.

A solution containing 0.10 mol/liter of 2-ethylnaphthalene, 0.19 mol/liter of cobaltic acetate and 1.5 mol/liter of trichloroacetic acid in acetic acid was kept at 25°C, without stirring, under a nitrogen atmosphere at atmospheric pressure. 71 % of the cobaltic ions had been reduced after 30 minutes. The analysis of the ether extract obtained as described in Example III showed that 57 % of the 2-ethylnaphthalene employed had been converted to yield the following oxidation products whose relative proportions are expressed as molar percentages :

| | |
|---|---|
| 2(1-hydroxyethyl)naphthalene (mainly in the form of its acetate ester) | 98 % |
| 2-acetylnaphthalene | 2 % |

EXAMPLE XXI

The experiment of the preceding example was repeated at 0°C, instead of at 25°C, while employing propionic acid instead of acetic acid as a solvent. 43 % of the cobaltic ions had been reduced after five hours, and analysis showed that 21 % of the 2-ethylnaphtalene employed had been converted to yield the following oxidation products whose relative proportions are expressed as molar percentages :

| | |
|---|---|
| 2-(1-hydroxyethyl)naphthalene (mainly in the form of its propionate ester) | 82 % |
| 2-acetylnaphthalene | 18 % |

EXAMPLE XXII

This example illustrates the possibility of operating at lower temperatures than 0°C.

A solution containing 0.51 mol/liter of 2-ethylnaphthalene, 0.18 mol/liter of cobaltic acetate and 1.5 mol/liter of trichloroacetic acid in propionic acid was kept at −20°C, without stirring, under an atmosphere of nitrogen at atmospheric pressure. 47 % of the cobaltic ions had been reduced after 5 hours, and analysis showed that 5 % of the 2-ethylnaphthalene employed had been converted to yield the following oxidation products whose relative proportions are expressed as molar percentages:

| | |
|---|---|
| 2-(1-hydroxyethyl)naphthalene (mainly in the form of its propionic ester) | 94 % |
| 2-acetylnaphthalene | 6 % |

EXAMPLE XXIII

This example illustrates the oxidation of p-chlorotoluene by means of the system consisting of manganic acetate and sulphuric acid.

A solution containing 0.10 mol/liter of p-chlorotoluene, 0.21 mol/liter of manganic acetate and 1.0 mol/liter of sulphuric acid in acetic acid was kept at 25°C, without stirring, under a nitrogen atmosphere at atmospheric pressure. 87 % of the manganic ions had been reduced after 2 hours. The analysis of ether extract obtained as described in Example III showed that 62 % of the p-chlorotoluene employed had been converted to yield the following oxidation products whose relative proportions are expressed as molar percentages:

| | |
|---|---|
| p-chlorobenzyl alcohol (mainly in the form of its acetate ester) | 74 % |
| p-chlorobenzaldehyde | 26 % |

EXAMPLE XXIV

This example illustrates the oxidation of p-methoxytoluene by means of the system consisting of cobaltic acetate and trichloroacetic acid.

A solution containing 0.10 mol/liter of p-methoxytoluene, 0.21 mol/liter of cobaltic acetate and 1.5 mol/liter of trichloroacetic acid was kept at 25°C, without stirring, under a nitrogen atmosphere at atmospheric pressure. 88 % of the cobaltic ions had been reduced after 5 minutes. The analysis of the ether extract obtained as described in Example III showed that 56 % of the p-methoxytoluene employed had been converted to yield the following oxidation products whose relative proportions are expressed as molar percentages:

| | |
|---|---|
| p-methoxybenzyl alcohol (mainly in the form of its acetate ester) | 82 % |
| p-methoxybenzaldehyde | 18 % |

EXAMPLE XXV

This example illustrates the oxidation of m-nitrotoluene by means of the system consisting of cobaltic acetate and trichloroacetic acid.

A solution containing 0.50 mol/liter of m-nitrotoluene, 0.19 mol/liter of cobaltic acetate and 1.5 mol/liter of trichloroacetic acid in acetic acid was kept at 25°C, without stirring, under a nitrogen atmosphere at atmospheric pressure. 51 % of the cobaltic ions had been reduced after 3 hours. The analysis of the ether extract obtained as described in Example III enabled to identify the following oxidation products whose relative proportions are expressed as molar percentages:

| | |
|---|---|
| m-nitrobenzyl alcohol (mainly in the form of its acetate ester) | 90 % |
| n-nitrobenzaldehyde | 10 % |

EXAMPLE XXVI

This example illustrates the oxidation of p-xylene by means of the system consisting of cobaltic acetate and trichloroacetic acid, in the presence of oxygen.

A solution containing 0.05 mol/liter of p-xylene, 0.20 mol/liter of cobaltic acetate and 1.5 mol/liter of trichloroacetic acid was stirred at 25°C in the presence of pure oxygen at atmospheric pressure. 19 % of the cobaltic ions had been reduced after 24 hours. The reaction mixture was then diluted with an equal volume of ether. An insoluble residue was filtered, washed for a first time with a mixture of acetic acid and ether (1/1), a second time with water, then dried. The infrared spectrum of the product thus isolated was identical to that of pure terephtalic acid and its acidity amounted to 11.98 meq./g (theoretical value : 12.04). On the other hand, the ether filtrates were collected before being treated and analyzed as described in Example III. It was thus established that 59 % of the p-xylene employed had been converted to yield the following oxidation products whose relative proportions are expressed as molar percentages:

| | |
|---|---|
| terephtalic acid | 71 % |
| p-toluic acid | 29 % |

EXAMPLE XXVII

This example illustrates the oxidation of m-diethylbenzene by means of the system consisting of manganic acetate and sulphuric acid.

A solution containing 0.05 mol/liter of m-diethylbenzene, 0.22 mol/liter of manganic acetate and 1.0 mol/liter of sulphuric acid in acetic acid was kept at 25°C under a nitrogen atmosphere at atmospheric pressure. 63 % of the manganic ions had been reduced after 30 minutes. The reaction mixture was then diluted with a saturated solution of sodium chloride in water, then subjected to repeated extractions with ether. The ether extract was neutralized by an aqueous solution of sodium carbonate and dried over anhydrous sodium sulphate before being analyzed by vapor phase chromatography. Analysis showed that the total quantity of the m-diethylbenzene employed had been converted, yielding the following oxidation products the relative proportions of which are expressed as molar percentages:

| | |
|---|---|
| m-(1-hydroxyethyl)ethylbenzene (mainly in the form of its acetate ester) | 78 % |
| m-bis(1-hydroxyethyl)benzene (in the form of its diacetate ester) | 18 % |
| m-ethylacetophenone | 4 % |

-continued

By operating under the same conditions but omitting sulphuric acid, only 0.2 % of the manganic ions were reduced after one hour (that being twice the time necessary hereinabove) and no oxidation products were detectable by analysis.

EXAMPLE XXVIII

The experiment of Example XXVII was repeated, except that the concentration of manganic acetate was increased by approximately 30 per cent (0.28 mol/liter instead of 0.22) and the reaction was extended to a total period of 20 hours. With these conditions, 97 % of the manganic ions were reduced and the oxidation products were shown to be distributed, in mols, in the following manner:

| | |
|---|---|
| m-bis(1-hydroxyethyl)benzene (in the form of its diacetate ester) | 61 % |
| m-(1-hydroxyethyl)ethylbenzene (mainly in the form of its acetate ester) | 16 % |
| m-ethylacetophenone | 21 % |
| m-diacetylbenzene | 2 % |

Compared to those of Example XXVII, these results show that, by increasing the quantity of oxidant in comparison to the substrate and by extending the reaction time, it is possible to oxidize the two alkyl substituents of a dialkylaromatic compound.

EXAMPLE XXIX

The experiment of Example XXVII was repeated except that the concentration of m-diethylbenzene was doubled (0.10 mol/liter instead of 0.05). The reaction was extremely fast, since 77 % of the manganic ions were reduced within three minutes.

The reaction mixture was then treated by an extraction method analogous to that applied in Example XXVII, and also analyzed by vapor phase chromatography. Analysis showed that 85 % of the m-diethylbenzene employed had been converted to yield the following oxidation products whose relative proportions are expressed as molar percentages:

| | |
|---|---|
| m-(1-hydroxyethyl)ethylbenzene (mainly in the form of its acetate ester) | 96 % |
| m-bis(1-hydroxyethyl)benzene (mainly in the form of its diacetate ester) | 3 % |
| m-ethylacetophenone | 1 % |

Compared to those of Example XXVII, these results show the gain in reaction rate and in selectivity achieved when increasing the amount of substrate compared to the oxidant.

EXAMPLE XXX

This example illustrates the oxidation of m-diethylbenzene by means of the system consisting of manganic acetate and perchloric acid.

The experiment of Example XXVII was repeated while substituting perchloric acid for sulphuric acid in the same concentration. 28 % of the manganic ions had been reduced after ten minutes. The reaction mixture was then treated and analyzed as in Example XXVII. It was thus established that 76 % of the m-diethylbenzene employed had been converted to yield the following oxidation products whose relative proportions are expressed as molar percentages:

| | |
|---|---|
| m-(1-hydroxyethyl)ethylbenzene (mainly in the form of its acetate ester) | 97 % |
| m-bis(1-hydroxyethyl)benzene (in the form of its diacetate ester) | traces |
| m-ethylacetophenone | 3 % |

EXAMPLE XXXI

This example illustrates the oxidation of m-diethylbenzene by means of the system consisting of cobaltic acetae and sulphuric acid.

A solution containing 0.05 mol/liter of m-diethylbenzene, 0.20 mol/liter of cobaltic acetate and 0.5 mol/liter of sulphuric acid in acetic acid was kept at 25° C under a nitrogen atmosphere at atmospheric pressure. 44 % of the cobaltic ions had been reduced after 20 minutes. The reaction mixture was then treated and analyzed as in Example XXVII. It was thus established that 55 % of the m-diethylbenzene employed had been converted to yield the following oxidation products whose relative proportions are expressed as molar percentages:

| | |
|---|---|
| m-(1-hydroxyethyl)ethylbenzene (mainly in the form of its acetate ester) | 70 % |
| m-bis(1-hydroxyethyl)benzene (in the form of its diacetate ester) | 4 % |
| m-ethylacetophenone | 24 % |
| m-(1-hydroxyethyl)acetophenone | 2 % |

EXAMPLE XXXII

This example illustrates the oxidation of m-diethylbenzenel by means of the system consisting of cobaltic acetate and phosphoric acid.

The experiment of Example XXXI was repeated while substituting phosphoric acid for sulphuric acid in the same concentration. 30 % of the cobaltic ions had been reduced after ten minutes, and analysis showed that 39 % of the m-diethylbenzene employed had been converted to yield the following oxidation products whose relative proportions are expressed as molar percentages:

| | |
|---|---|
| m-(1-hydroxyethyl)ethylbenzene (mainly in the form of its acetate ester): | 79 % |
| m-bis(1-hydroxyethyl)benzene (in the form of its diacetate ester) | 6 % |
| m-ethylacetophenone | 15 % |

EXAMPLE XXXIII

This example illustrates the oxidation of m-diethylbenzene by means of the system consisting of cobaltic acetate and perchloric acid.

The experiment of Example XXXI was repeated while substituting perchloric acid at the concentration of 1.0 mol/liter for sulphuric acid. 47 % of the cobaltic ions had been reduced after ten minutes, and analysis showed that 79 % of the m-diethylbenzene employed had been converted to yield the following oxidation products whose relative proportions are expressed as molar percentages:

| | |
|---|---|
| m-(1-hydroxyethyl)ethylbenzene (mainly in the form of its acetate ester) | 86 % |
| m-bis(1-hydroxyethyl)benzene (in the form of its diacetate ester) | 4 % |
| m-ethylacetophenone | 10 % |

EXAMPLE XXXIV

This example illustrates the oxidation of m-diethylbenzene by the system consisting of cobaltic acetate and trichloroacetic acid.

The experiment of Example XXXI was repeated while substituting trichloroacetic acid at the concentration of 1.5 mol/liter for sulphuric acid. 23 % of the cobaltic ions had been reduced after 30 minutes, and analysis showed that 42 % of the m-diethylbenzene employed had been converted to yield the following oxidation products whose relative proportions are expressed as molar percentages:

| | |
|---|---|
| m-(1-hydroxyethyl)ethylbenzene (mainly in the form of its acetate ester) | 90 % |
| m-bis(1-hydroxyethyl)benzene (in the form of its diacetate ester) | 3 % |
| m-ethylacetophenone | 7 % |

By operating in the same conditions but in the absence of trichloroacetic acid, only 10 % of the cobaltic ions were reduced after two hours (this being a period which is four times as long as in the experiment hereinabove) and only 9 % of the m-diethylbenzene was converted to yield the following products:

| | |
|---|---|
| m-(1-hydroxyethyl)ethylbenzene (in the form of its acetate ester) | 36 % |
| m-ethylacetophenone | 64 % |

Hereagain, it is apparent that in the absence of the acid activator, the reaction is not only slowed down considerably, but its selectivity is changed completely.

EXAMPLE XXXV

This example illustrates the influence of oxygen on the oxidation of m-diethylbenzene by means of the oxidizing system used in the preceding example.

The experiment of Example XXXIV was repeated, but this time while stirring the reaction mixture in the presence of pure oxygen at atmospheric pressure. 17 % of the cobaltic ions had been reduced after 30 minutes, and analysis showed that 44 % of the m-diethylbenzene employed had been converted to yield the following oxidation products whose relative proportions are expressed as molar percentages:

| | |
|---|---|
| m-ethylacetophenone | 66 % |
| m-(1-hydroxyethyl)ethylbenzene | 17 % |
| acetate ester of m-(1-hydroxyethyl)ethylbenzene | 16 % |
| m-bis(1-hydroxyethyl)benzene | 1 % |

By continuing the same experiment up to 24 hours, 57 % of the cobaltic ions were reduced and 89 % of the m-diethylbenzene employed was converted to yield the following products:

| | |
|---|---|
| m-ethylacetophenone | 73 % |
| m-(1-hydroxyethyl)ethylbenzene | 2 % |
| acetate ester of m-(1-hydroxyethyl)ethylbenzene | 10 % |
| m-bis(1-hydroxyethyl)benzene | 5 % |
| m-(1-hydroxyethyl)acetophenone | 3 % |
| m-diacetylbenzene | 7 % |

By comparing these results to those of Example XXXIV, it is apparent that in the presence of oxygen the hydrocarbon is oxidized preferentially into ketone rather than into alcohol.

EXAMPLE XXXVI

This example illustrates the oxidation of the acetate of m-(1-hydroxyethyl)ethylbenzene by means of the system consisting of cobaltic acetate and phosphoric acid.

A solution containing 0.05 mol/liter of the acetate of m-(1-hydroxyethyl)ethylbenzene, 0.10 mol/liter of cobaltic acetate and 1.0 mol/liter of phosphoric acid was kept at 25° C under a nitrogen atmosphere at atmospheric pressure. 43 % of the cobaltic ions had been reduced after 4 hours. The reaction mixture was then treated by an extraction method analogous to that employed in Example XXVII and the extract was also analyzed by vapor phase chromatography. It was thus established that 25 % of the ester employed had been converted to yield the following oxidation products whose relative proportions are expressed as molar percentages:

| | |
|---|---|
| m-bis(1-hydroxyethyl)benzene (mainly in the form of its diacetate ester) | 95 % |
| m-ethylacetophenone | 3 % |
| m-(1-hydroxyethyl)acetophenone | 2 % |

These results combined with those of Examples XXIX to XXXIV show that it may be advantageous to operate in two consecutive stages, instead of in one operation as in Example XXVIII, in order to oxidize the two substituents of a dialkyl aromatic compound by the process of the invention.

EXAMPLE XXXVII

This example illustrates the oxidation of durene by means of the system consisting of cobaltic acetate and trichloroacetic acid.

A solution containing 0.05 mol/liter of durene, 0.30 mol/liter of cobaltic acetate and 1.5 mol/liter of trichloroacetic acid in acetic acid was stirred at 60° C in the presence of pure oxygen under a pressure of 10 kg/cm2. 78 % of the cobaltic ions had been reduced after 24 hours. After evaporation of the solvent, the acidic products were separated by extraction with aqueous potash followed by acidification with hydrogen chloride; they were then established by paper chromatography. It was thus established that durene had been quantitatively converted to yield the following oxidation products whose relatively proportions are expressed as molar percentages:

| | |
|---|---|
| Durylic acid | 4% |
| Dimethylphthalic acids | 68% |
| Methyltrimellitic acid | 23% |
| Pyromellitic acid | 5% |

EXAMPLE XXXVIII

Into a corrosion-resistant autoclave equipped with a mechanical agitation device, a heating jacket, a cooling coil, a gas inlet tube and a vent, there were charged 0.100 mole of durene and 400 ml of a solution containing 0.250 mole of cobaltic acetate and 0.625 mole of perfluorocaprylic acid in acetic acid. The concentration of the cobaltic salt in this solution was therefore about 0.6 mole per liter and the molar ratio of perfluorocaprylic acid to cobaltic salt was 2.5.

Air was admitted into the solution at a rate of 100 liters per hour while stirring and maintaining the pressure at 10 Kg. per $cm^2$. In order to maintain a high level of cobaltic ions throughout the reaction, acetaldehyde was fed into the reaction mixture at a rate of 20 ml per hour of a 50 volume % solution in acetic acid. The mixture was heated progressively for about 1 hour up to a temperature of 60°C and then was maintained at this temperature for further time of five hours.

At the end of the run, the reaction mixture was cooled and withdrawn after depressurization of the autoclave. The cobaltic ions present therein were reduced by treatment with an aqueous solution of a ferrous salt. The resulting mixture was then evaporated to dryness and the residue treated with aqueous alkali. Precipitated metals were removed by centrifugation and the clear alkaline solution was analyzed for aromatic acids by a method combining paper chromatography and UV spectrophotometry. It was thus determined that 76% of the starting durene had been transformed into pyromellitic acid and 24% into methyltrimellitic acid. Thus, both acids exactly account for the durene feed which demonstrates that no overoxidation had taken place.

In another experiment, the same procedure was repeated except that acetaldehyde was omitted. No pyromellitic acid was detected in the reaction mixture, the only products being durylic acid and dimethylphthalic acids. This result shows the necessity of regenerating cobaltic ions during the reaction for ensuring efficient oxidation by the present process.

Moreover, in order to demonstrate the specific efficacy of the perfluorinated compounds, the procedure of Example XXXVIII was repeated except that perfluorocaprylic acid was omitted. After standing overnight, the reaction mixture was centrifuged to separate a precipitate which was washed by reslurrying in acetic acid and dried under vacuum. 46.8 grams of dark green powder was thus obtained, the analysis of which revealed the presence of cobalt (21 weight per cent) pyromellitic acid (26 weight per cent) and methyltrimellitic acid (5 weight per cent). The combined supernatent and washing were treated and analyzed by the procedure of Example XXXVIII to determine the aromatic acids not precipitated. From both analyses it was determined that 54% of the starting durene had been transformed into pyromellitic acid and 34% into methyltrimellitic acid. The remaining 12 per cent could not be accounted for by any other product and is considered as the amount of material lost as a result of overoxidation.

By comparing these results with those of Example XXXVIII, it appears clearly that the presence of perfluorocaprylic acid during the oxidation of durene by cobaltic acetate not only enhances the reaction rate but also improves the selectivity of the reaction for polycarboxylic acids while impeding the formation of cobalt complexes.

EXAMPLE XXXIX

The procedure of Example XXXVIII was repeated and the reaction mixture was filtered after standing overnight. A small precipitate was thus isolated which was washed by reslurrying in hot acetic acid. After drying under vacuum for about 4 hours at 100°C, the resulting white solid was analyzed and shown to be pure pyromellitic acid.

The combined filtrate and washings were then evaporated to a volume of 400 ml. The resulting solution was recycled into the autoclave and admixed therein with a new charge of 0.100 mole of durene. The mixture was then oxidized exactly as described in Example XXXVIII and again filtered. This time an important precipitate was recovered which was washed and dried as described hereabove. Again it was shown to contain nothing but pyromellitic acid.

This procedure was repeated with almost identical results up to a total of 17 successive operations. The amount of pyromellitic acid recovered in each operation as a precipitate was nearly constant and averaged 0.091 mole. The molar yield in pyromellitic acid based on durene feed was therefore 91% which corresponds to a yield in weight of 172%.

EXAMPLE XL

The procedure of Example XXXVIII was repeated except that the reaction mixture was heated up to 80°C instead of 60°C. In these conditions 90% of starting durene was transformed into pyromellitic acid and 10% into methyltrimellitic acid.

These results show that by the process of the present invention durene can be extensively transformed into pyromellitic acid in one step. Moreover, they show that even at 80°C the amount of polycarboxylic acids formed from durene account exactly for the latter i.e. overoxidation is nil. By working at about the same temperature in the absence of perfluorocaprylic acid, overoxidation mounted to 38% and the yield in pyromellitic was only 42%.

EXAMPLE XLI

The procedure as disclosed in Example XXXVIII was repeated except that instead of passing continuously air through the reaction mixture, pure oxygen was supplied by intermittent pressurization of the autoclave from 5 to 10 kg. per cm². By treating and analyzing the reaction mixture as in Example XXXVIII, it was determined that 71% of the starting durene had been transformed into pyromellitic acid and 29% into methyltrimellitic acid.

EXAMPLE XLII

The procedure of Example XLI was repeated except that heptafluorobutyric acid was substituted for perfluorocaprylic acid. 64% of the starting durene was transformed into pyromellitic acid and 32% into methyltrimellitic acid.

EXAMPLE XLIII

The procedure of Example XLI was repeated except that trifluoroacetic acid was substituted for perfluorocaprylic acid. 62% of the starting durene was transformed into pyromellitic acid and 32% into methyltrimellitic acid.

By substituting trichloroacetic acid for trifluoroacetic acid the amounts of pyromellitic and methyltrimellitic acids were respectively 49% and 45% of the durene feed. These results, when compared to the preceding ones, clearly show the superiority of perfluorinated over perchlorinated acids.

EXAMPLE XLIV

The procedure of Example XXXVIII was repeated except that 0.150 mole of pseudocumene was substituted for the 0.100 mole of durene. After standing overnight, the reaction mixture was filtered to separate a small precipitate which was washed and dried. The resulting white solid was analyzed and shown to be pure trimellitic acid. The combined filtrate and washings were treated and analyzed by the procedure of Example XXXVIII to determine the aromatic acids still in solution. From both analyses it was determined that 76% of the starting pseudocumene had been transformed into trimellitic acid and 18% into methylphthalic acids.

What is claimed is:

1. The process of oxidizing an alkyl carbocyclic aromatic compound having at least one methyl group directly linked to the aromatic nucleus, to selectively produce an aromatic acid, comprising reacting said alkyl carbocyclic aromatic compound in the liquid phase with a cobaltic salt in the presence of a molar excess with respect to said salt of an activator selected from the group consisting of the acids having a dissociation constant higher than $10^{-3}$ other than hydrogen halides and which are stable in the conditions of the reaction, boron trifluoride and mixtures thereof, at a temperature between −30°C and +100°C, and under a partial pressure of oxygen between 0.1 to 50 atmospheres.

2. The process of oxidizing an alkyl carbocyclic aromatic compound having at least one methyl group directly linked to the aromatic nucleus, to selectively produce an aromatic acid, comprising reacting said alkyl carbocyclic aromatic compound in the liquid phase with a cobaltic carboxylate in the presence of a molar excess with respect to said salt of an activator selected from the group consisting of the acids having a dissociation constant higher than $10^{-3}$ other than hydrogen halides and which are stable in the conditions of the reaction, boron trifluoride and mixtures thereof, at a temperature between −30°C and +100°C, and under a partial pressure of oxygen between 0.1 to 50 atmospheres.

3. The process as defined in claim 2 wherein the aromatic nucleus of said alkylaromatic compound is selected from the group consisting of benzene and naphthalene.

4. The process as defined in claim 3 wherein said aromatic nucleus has from 1 to 6 alkyl substituents each having from 1 to 4 carbon atoms.

5. The process as defined in claim 3 wherein said aromatic nucleus is further substituted with a polar radical selected from the group consisting of halo, nitro, acyl, 1-acyloxyalkyl, carboxy and alkoxy.

6. The process as defined in claim 2 wherein said cobaltic carboxylate is the salt of a fatty acid having from 2 to 10 carbon atoms.

7. The process as defined in claim 6 wherein the cobaltic salt is an acetate.

8. The process as defined in claim 2 wherein the reaction is effected in the presence of a solvent selected from the group consisting of the fatty acids having from 2 to 10 carbon atoms, and the methyl and t-butyl esters of said fatty acids.

9. The process as defined in claim 8 wherein said solvent is acetic acid.

10. The process as defined in claim 2 wherein the alkylbenzene is durene and the oxidation product is a member of the group consisting of durylic, dimethylphthalic, methyltrimellitic and pyromellitic acids.

11. Process for the preparation of pyromellitic acid from durene which comprises reacting durene in acetic acid with cobaltic acetate at a concentration of at least 0.2 mole per liter of reaction mixture and a ratio of cobaltic ions to total cobalt above 0.5, in the presence of trifluoroacetic acid, the molar ratio of said perfluorinated acid to said cobalt being at least 1, at a temperature comprised between 40°C and 100°C and in the presence of molecular oxygen at a partial pressure of 0.2 to 20 atmospheres, and recovering free pyromellitic acid from the reaction mixture.

12. The process of oxidizing an alkyl carbocylic aromatic compound having at least one methyl group directly linked to the aromatic nucleus, to selectively produce an aromatic acid, comprising reacting said alkyl carbocyclic aromatic compound in the liquid phase with a cobaltic carboxylate in the presence of a molar excess with respect to said salt of an activator selected from the group consisting of the acids selected from the group of sulfuric, perchloric, p-toluenesuphonic, trifluoroacetic, trichloroacetic, tribromoacetic, dichloroacetic, phosphoric and monochloroacetic acids, boron trifluoride and mixtures thereof, at a temperature between −30°C and +100°C, and under a partial pressure of oxygen between 0.1 and 50 atmospheres.

13. Process for the preparation of pyromellitic acid from durene which comprises reacting durene in acetic acid with cobaltic acetate at a concentration of at least 0.2 mole per liter of reaction mixture and a ratio of cobaltic ions to total cobalt above 0.5, in the presence of a perfluoroacetic acid selected from a group consisting of pentafluoroprop ionic acid, heptafluorbutyric acid and perfluorocaprylic acid, the molar ratio of said perfluoroacetic acid to said cobalt salt being at least 1, at a temperature comprised between 40°C and 100°C and in the presence of molecular oxygen at a partial pressure of 0.2 to 20 atmospheres and recovering free pyromellitic acid from the reaction mixture.

14. Process for the preparation of aromatic polycarboxylic acids having at least two carboxyl groups on vicinal nuclear carbon atoms from methylaromatic compounds having at least one methyl substituent on a nuclear carbon atom vicinal to another nuclear carbon atom substituted by a radical selected from the group consisting of methyl, hydroxymethyl, formyl and carboxyl radicals, which comprises reacting said methylaromatic compounds in acetic acid with a cobaltic salt at a concentration of at least 0.1 mole per liter of reaction mixture, the ratio of cobaltic ions to total cobalt being maintained above 0.5, in the presence of a member of the group consisting of pentafluoropropionic acid, heptafluorobutyric acid and perfluorocaprylic acid, the molar ratio of said perfluorinated compound to said cobaltic salt being at least 1, at a temperature comprised between 40°C and 100°C, and in the presence of molecular oxygen at a partial pressure of from 0.2 to 20 atmospheres.

15. Process according to claim 14 wherein both cobalt and perfluorinated acid are supplied as a cobaltic salt of the perfluorinated acid.

* * * * *